United States Patent [19]

Hallewell et al.

[11] Patent Number: 5,145,782
[45] Date of Patent: Sep. 8, 1992

[54] DNA EXPRESSION VECTOR SUITABLE FOR DIRECT EXPRESSION OF A FOREIGN GENE

[75] Inventors: Robert A. Hallewell, San Francisco; Jeffrey C. Edman, Davis; William J. Rutter; Howard M. Goodman, both of San Francisco, all of Calif.

[73] Assignee: The Regents of the University of California, Oakland, Calif.

[21] Appl. No.: 121,901

[22] Filed: Nov. 17, 1987

Related U.S. Application Data

[63] Continuation of Ser. No. 894,458, Aug. 4, 1986, abandoned, which is a continuation of Ser. No. 518,613, Jul. 29, 1983, abandoned, which is a continuation of Ser. No. 213,879, Dec. 8, 1980, abandoned.

[51] Int. Cl.$^5$ .................. C12N 15/71; C12N 15/00; C12P 21/00
[52] U.S. Cl. .................. 435/320.1; 435/69.1; 435/172.3; 435/252.3; 435/252.33; 536/27; 935/40; 935/41; 935/45
[58] Field of Search .................. 435/68, 70, 71, 91, 435/172.1, 172.3, 253, 320, 252.3, 252.31-252.35, 69.1, 69.3, 320.1; 536/27; 935/11, 12, 38, 39, 40, 41, 45

[56] References Cited

U.S. PATENT DOCUMENTS

| | | | |
|---|---|---|---|
| 4,332,892 | 6/1982 | Ptashne et al. | 435/68 |
| 4,418,149 | 11/1983 | Ptashne et al. | 435/252.3 |
| 4,663,283 | 5/1987 | Kleid et al. | 435/91 |

FOREIGN PATENT DOCUMENTS

| | | | |
|---|---|---|---|
| 0013828 | 6/1980 | European Pat. Off. | 435/172.3 |
| 2034323 | 4/1980 | United Kingdom | 435/172.3 |

OTHER PUBLICATIONS

Burrell et al; Nature 279: 43 (1979).
Bertrand, K. et al, *Science* 189:22-26 (1975) "New features of the Regulation of the Tryptophan Operon".
Bennett, G. N. et al, *Proc Natl Acad Sci (USA)* 73:2351-2355 (1976) "Nucleotide sequence of region preceding trp mRNA initiation site and its role in promoter and operator function".
Sutcliffe, J. G. et al, Plasmid Cloning Vectors in *Genetic Engineering* (1978) by CRC Press, Inc., pp. 83, 92, 94-96.
Roberts, J. R., *Methods in Enzymology* 68: 27-41 (1979), "Directory of Restriction Endonucleases".
Enger-Valk, B. E., *Gene* 9:69-85 (1980), "Construction of New Cloning Vehicles with Genes of the Tryptophan Operon of Escherichia coli as Genetic Markers".
Stauffer, G. V. et al, *Proc Natl Acad Sci (USA)* 75:4833-4837, "Single base-pair alterations in the *Escherichi coli* trp operon leader region that relieve transciption termination at the trp attenuator".
Fritsch, A. etal, *C. R. Acad. Sc. Pairs* Series D 287, 1453 (1978), "Virologie—Clonage du genome du virus de l'hepatite B dans *Escherichia coli*".
Watson, Molecular Biology of the Gene (3rd Edition), pp. 394-395.

*Primary Examiner*—James Martinell
*Attorney, Agent, or Firm*—Morrison & Foerster

[57] ABSTRACT

A DNA expression vector is described which is derived from the highly efficient trp operon. The expression vector provides for the direct expression of an inserted gene or cDNA. Using the expression vector described herein, it is possible to obtain the protein coded by the gene or cDNA directly and not as a fusion protein. The expression vector comprises the promoter, operator and leader ribosomal binding site of the trp operon.

4 Claims, 3 Drawing Sheets

DNA EXPRESSION VECTOR SUITABLE FOR DIRECT EXPRESSION OF A FOREIGN GENE

This application is a continuation of U.S. Ser. No. 894,458, filed Aug. 4, 1986 (abandoned), which is a continuation of U.S. Ser. No. 518,613, filed Jul. 29, 1983 (abandoned), which is a continuation of U.S. Ser. No. 213,879, filed Dec. 8, 1980 (abandoned).

BACKGROUND OF THE INVENTION

One of the goals of recombinant DNA technology is to obtain efficient expression of the cloned DNA. It is desirable to obtain the expression product in as high yields as possible. Several possible techniques for expression are available as options, and may include (a) modification of the coding sequences to provide an exact desired translational starting point; (b) selection or construction of an optimal expression vector; (c) post-translational processing, either by exploiting in vivo processing activity of the host or by in vitro chemical means; and (d) direct expression.

Cloned DNA can be expressed as a fusion protein which contains the protein coded for by the cloned DNA as the C-terminal end. The protein coded for by the foreign gene or cDNA can be expressed as a fusion protein by insertion of the foreign gene or cDNA into appropriate sites within expressed operons (expression vectors) including, for example, the Pst I site in the β-lactamase gene of pBR322 (Villa-Komaroff, L., et al, *Proc. Nat. Acad. Sci. USA*, 75, 3727 (1978) and Seeburg, P., et al, *Nature*, 274, 795 (1978)), the EcoRI site of pBR322 carrying the lac control region and coding sequence for β-galactosidase (Itakura, K., et al, *Science*, 198, 1056 (1977)) or the HindIII site of the trpD gene of plasmid ptrpED50 (Martial, J., et al, *Science*, 205, 602 (1979)). Modifications of sequence length, if needed, by one or two nucleotides in order to achieve correct reading frame phase are well known in the art.

Cloned DNA can be expressed directly under certain circumstances. Chang, A.C.Y., et al, *Proc. Nat. Acad. Sci. USA*, 77, 1442 (1980) have reported that they obtained direct expression of mouse dihydrofolate reductase (DHFR). The mouse DHFR coding sequence had been dC-tailed and inserted into the dGtailed, Pst I site of pBR322. The authors found that transformed bacteria synthesized a protein having enzymatic properties, immunological reactivity and molecular size of the mouse DHFR. They also found that the cDNA for DHFR was in a different translation reading frame from the bacterial β-lactamase gene into which it had been inserted. These findings implied that translation was re-initiated at the start codon for the mouse DHFR under these circumstances, i.e., method of insertion, to produce mouse DHFR directly and not as part of a fusion protein.

A second technique for direct expression involves replacing the coding segment normally transcribed and translated by the bacterial control region. The essential component of the control region to be preserved is termed the expression unit, which includes a promoter and a ribosomal binding site capable of acting in the host organism. It is not necessary to remove all of the nucleotides coding for the host portion of the fusion protein. Optimal protein expression is dependent on the distance and sequence between the ribosomal binding site and the start codon (AUG) of the protein to be expressed. Goeddel, I. et al, *Nature* 281, 544 (1979); Roberts, T. M. et al, *Proc. Natl. Acad. Sci. USA* 76, 5596 (1979); and Taniguchi, T. et al, *Proc. Natl. Acad. Sci. USA* 77, 5230 (1980). Although the exact distance for optimal protein expression is not known, it has been reported that the start codon may be located anywhere within 3-11 nucleotides of the ribosomal binding site. Shine, J., et al, *Proc. Nat. Acad. Sci. USA*, 71, 1342 (1974) and Steitz, J., et al, *Proc. Nat. Acad. Sci. USA*, 72, 4734 (1975). In this 3-11 nucleotide region, the first AUG to be encountered sets the reading frame for translation. In the case of ptrpE30, derived from ptrpED50, described supra, and containing the operator, promoter, leader, attenuator and ribosome binding sequence of the E protein of the tryptophan operon together with the nucleotide sequence coding for seven amino acids of the trp E protein followed by a HindIII site, the removal of a minimum of 23-29 nucleotides from the HindIII site provides a site for insertion of the cDNA insert under tryptothan operon control. In this method, the foreign DNA is prepared so that it begins at or near the start codon. This DNA is then inserted into the modified ptrpE30 to obtain direct expression of the insert DNA.

The trp operon has proved useful for the expression of a fusion protein or for direct expression. Several expression vectors containing the trp operon have been prepared for use in synthesizing fusion proteins. Hallewell, R. A. and Emtage, R. A., *Gene*, 9, 27 (1980) describe the preparation of an expression vector, ptrpED5-1, containing the promoter, operator, leader, attenuator, trp E gene and 15% of the trp D gene sequences. This expression vector has been utilized to produce a fusion protein containing human growth hormone (Martial, J., et al, supra). Tacon, W., et al, *Molec. Gen. Genet.*, 177, 427 (1980) describe the preparation of expression vectors pWT 111, pWT 121 and pWT 131. These expression vectors are derived from ptrpED5-1 by digestion with HinfI to remove the DNA sequences of the trp D gene and all but 21 deoxyribonucleotide of the trp E gene.

In each of the above expression methods utilizing the trp operon, maximum expression is not obtainable. The trp operon contains two transcriptional control points. The primary control point is the promoter/operator region. Transcription of the operon is regulated by trp repressor molecules binding at this site and repressing the operon. The addition of 3β-indolylacrylic acid induces the trp operon approximately 50-fold. A secondary control point involves the leader and attenuator sequence of the operon. This sequence regulates transcription of the trp operon by approximately 10-fold, by terminating transcription at this point (Bertrand, K., et al, *Science*, 189, 22 (1975)). The leader is a potentially translatable region for a peptide of 14 amino acids. It possesses its own ribosome binding site and a coding sequence containing two tandem trp codons. The mechanism of attenuation appears to involve secondary structure changes in the nascent messenger that are influenced by the translation of these two codons. Lee, F., and YANOFSKY, C., PROC. NATL, *ACAD. SCI. USA*. 75, 5988-5992 (1978).

When trp tRNA is limiting, translation pauses at these two codons and transcription continues past the attenuator. However, when trp tRNA is abundant, translation continues and transcription terminates at the attenuator, yielding a 140 bp transcript corresponding to the leader region.

While it is possible to induce the trp operon 50-fold with 3β-indolylacrylic acid, it is not possible to maximize transcription and hence expression when the trp operon expression vector contains the attenuator sequence. Applicants have prepared an expression vector derived from the trp operon which maximizes expression of the foreign gene and provides for the direct expression of the foreign gene.

SUMMARY OF THE INVENTION

The present invention discloses a DNA expression vector which is derived from the trp operon. The expression vector provides for the direct expression of inserted, foreign DNA. The expression vector comprises the promoter, operator and leader ribosomal binding site of the trp operon.

The expression vector, identified as ptrpL1, is prepared by isolating the DNA sequence containing the promoter, operator and leader ribosomal binding site by suing appropriate restriction endonucleases. This DNA sequence is then inserted into an appropriate plasmid to produce the expresssion vector, ptrpL1.

DETAILED DESCRIPTION OF THE INVENTION

Throughout this description the following nomenclature is utilized. a plasmid containing the trp operon is designated ptrp. The amount of the trp operon included in the plasmid is the next part of the designation. Thus, "E" refers to the sequence through part of the E gene; "ED" refers to the sequence through part of the D gene; and "L" refers to the sequence through the leader ribosomal binding site. The first number which appears after these "E", "ED" of "L" designations identifies the colony from which the plasmid was isolated. The second number, −1, 0 or +1, when it appears, refers to the reading frame at the insertion site. The "0" designation means that the reading frame is in phase with the start codon.

The trp operon has been well studied. The operon contains a HinfI fragment which comprises 490 base pairs containing the sequence for the promoter, operator, leader ribosomal binding site, leader, attenuator and first seven amino acids of the E gene (Lee, F., et al, *J.Mol.Biol.* 121, 193 (1978)). A single HpaI site in the trp promoter exists within this fragment (Brown, K. D., et al, *J.Mol.Biol.* 121, 153 (1978)). The nucleotide sequence for the HpaI-HinFI fragment is shown in Lee, F. et al, supra. Bennet, G. N., et al, *Proc. Nat. Acad. Sci. USA* 73, 2351 (1976) shows the nucleotide sequence for the area of the trp operon extending approximately 20 base pairs 5' of the HpaI site through approximately 35 base pairs 3' of the HpaI site. These references show the following nucleotide sequence of the plus strand for the region of interest of the trp operon including the HpaI and TaqI restriction endonuclease sites:

polymerase I and the appropriate deoxyribonucleotide. A linker nucleotide sequence containing the restriction sequence for HindIII endonuclease is blunt-end ligated to the filled in HinfI fragment by the procedure of Valenzuela, et al, *Nature* 280, 815 (1979). Insertion of this fragment into pBR322 is accomplished by following the procedure of Ullrich, A., et al, *Science* 196, 1313 (1977). This mixture is then used to transform a suitable host, such as *E. coli* X1776, RR1, HB101 or other bacteria as described by Seeburg, P. H., et al, *Nature* 270, 486 (1977) and colonies are selected on ampicillin, A recombinant clone with the trp promoter directed towards the β-lactamase gene is obtained by screening DNA miniscreens for a 200 base pairs HpaI-EcoRI fragment. This procedure involves isolating and analyzing the DNA from colonies of transformed bacteria. This plasmid is designated as ptrpE2-1.

Figure 1:
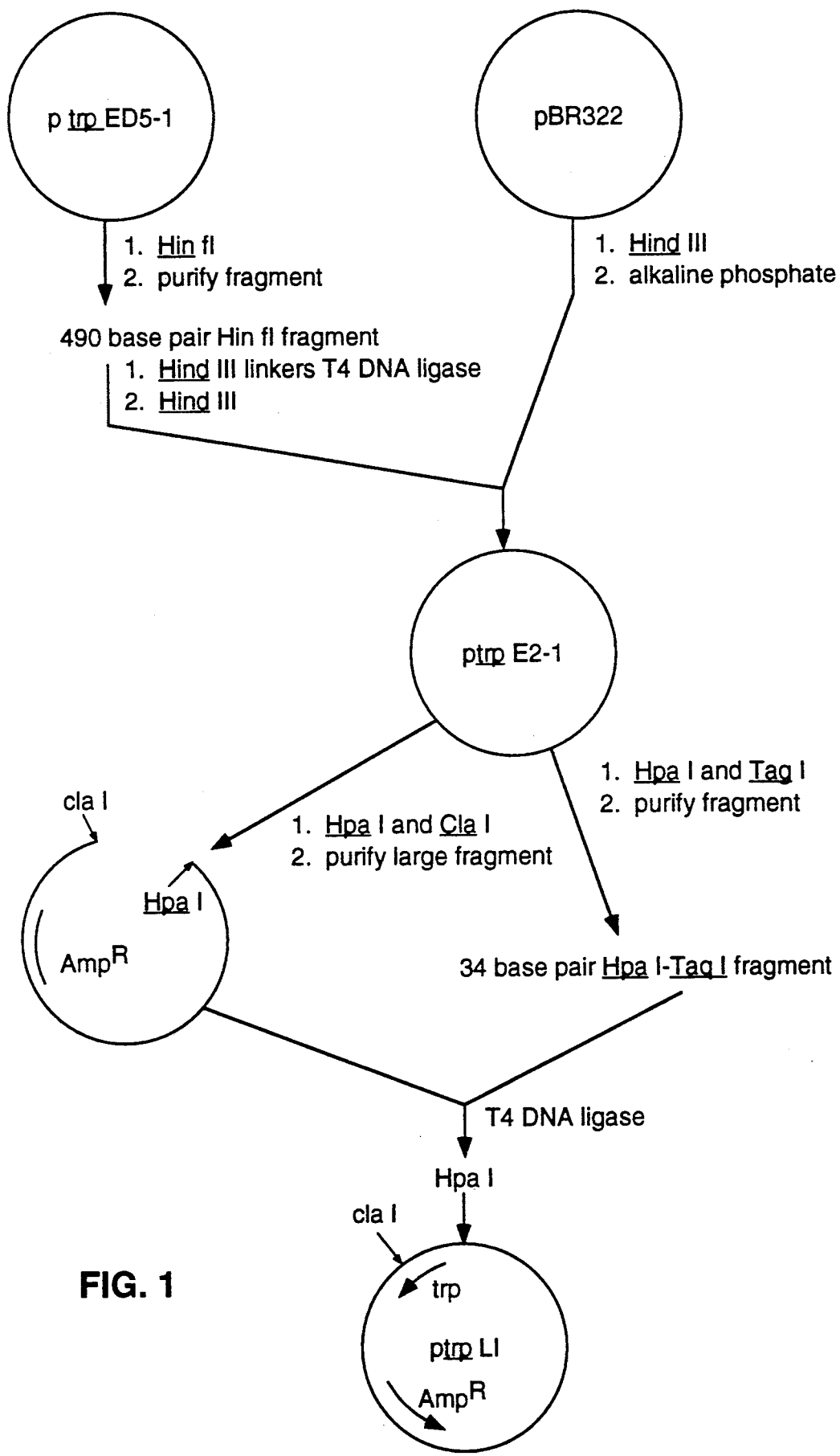

The plasmid ptrpE2-1 is digested with a mixture of HpaI and ClaI restriction endonucleases to remove approximately 180 base pairs. This removes part of the promoter, the operator, leader, attenuator and E gene sequences. A second portion of plasmid ptrpE2-1 is digested with a mixture of HpaI and TaqI restriction endonucleases to remove a HpaI-TaqI fragment comprising 34 base pairs. This sequence contains part of the promoter, the operator and leader ribosomal binding site. This fragment is isolated and purified by preparative gel electrophoresis. The HpaI-TaqI fragment is ligated with the HpaI-ClaI restricted ptrpE2-1 using a 3-fold molar excess of said fragment and T4 DNA ligase, essentially as described by Ullrich et al, supra. The resulting plasmid is used to transform a suitable host, such as E. coli X1776, RR1, HB101 or other bacteria and colonies are selected on ampicillin. A recombinant clone is obtained by screening DNA miniscreens for a 34 base pairs HpaI-ClaI fragment. This plasmid is designated ptrpL1. FIG. 1 illustrates the method of forming ptrpL1.

The plasmid pBR322 contains a single ClaI site which is conserved in ptrpE2-1. ClaI recognizes and cleaves the hexanucleotide sequence $$AT\downarrow CGAT$$
$$TAGC\uparrow AT$$

and TaqI recognizes and cleaves the sequence $$T\downarrow CGA$$
$$AGC\uparrow T.$$

Thus, it is possible to clone a TaqI fragment into the ClaI site. Similarly, restriction with HpaII or AcyI results in fragments having a 5'-CG overlap which can also be cloned into the ClaI site. The HpaI-TaqI frag-

```
    TaqI         HpaI                                    TaqI
5'... TCGAACTAGTTAACTAGTACGCAAGTTCACGTAAAAAGGGTATCGACAATG ... 3'
            Pribnow box                leader              start condon-
                                       ribosomal           leader
                                       binding site        peptide
```

The present invention utilizes these restriction sites in the preparation of ptrpL1.

The 490 base pair HinfI fragment of the trp operon is obtained by digesting plasmid ptrp ED5-1 with HinfI restriction endonuclease. The protruding 5' ends are filled in with the use of the Klenow fragment of DNA ment contains deoxyadenosine before the TaqI sequence, it is possible to recreate the ClaI site when the HpaI-TaqI fragment from ptrpE2-1 is ligated into the HpaI-ClaI digested ptrpE2-1. The ClaI site is located three base pairs to the 3' side of the leader ribosomal binding site of ptrpL1. The ClaI site is suitable for the insertion of foreign DNA into the expression vector. If the start codon of the foreign DNA appears within 50 nucleotides of the leader ribosomal binding site or within 13–16 nucleotides thereof, direct expression of the foreign DNA may occur. Shine, J., et al, supra, and Steity, J., et al, supra. The plasmid ptrpL1 has been found to be a useful expression vector for the direct expression of foreign DNA.

Foreign DNA having a start codon is inserted into the ClaI site of ptrpL1. The foreign DNA is first modified, if necessary, to remove most of the 5'-untranslated region. This is accomplished either by controlled digestion of the 3' end of the insert using the 3' exonuclease of T4 DNA polymerase or by the combination restriction endonuclease cleavage at a point to the 5' side of the desired starting point and chemical synthesis to restore that portion of the desired sequence thus removed. For further details of these procedures, see copending application Ser. No. 125,878, filed Feb. 25, 1980, incorporated herein by reference. By following these procedures, a foreign DNA sequence lacking most of the 5'-untranslated region is obtained. In general, digestion is performed so that only 5–20 base pairs remain in the 5'-untranslated region. A linker nucleotide sequence containing the restriction sequence for BamHI endonuclease which also contains the restriction sequence for HpaII endonuclease is blunt-end ligated to the modified foreign DNA by the procedure of Valenzuela, et al, supra. Since both HpaII and ClaI leave a 5' extension of CG, the foreign gene can then be inserted into the ClaI site of ptrpL1. The modified foreign DNA is then digested with HpaII and ptrpL1 is digested with ClaI. The two are ligated together using T4 DNA ligase essentially as described by Ullrich et al, supra. Host bacteria, such as *E. coli*, X1776, RR1, HB101 or other bacteria are transformed by the expression vector containing the foreign DNA. Transformants are selected for ampicillin resistance and grown under conditions suitable for expression of the foreign DNA. Expression of the foreign DNA can be seen by new translational products not seen in non-transformed bacteria or uninduced bacteria.

The details of the present invention will be further described by the following examples. In these examples, digestions with restriction endonucleases were carried out under conditions optimized for each enzyme. Restriction endonucleases, their nomenclature and site specificity, have been described in detail by Roberts, R., *Nucleic Acids Res.* 8, r63–r80 (1980). Enzymes were obtained commercially (New England BioLabs, Cambridge, Mass.) and optimal conditions according to supplier's recommendations were employed unless noted otherwise. T4 DNA ligase was obtained from New England BioLabs. The use of T4 DNA ligase and suitable reaction conditions have been previously described by Valenzuela et al, supra and Ullrich et al, supra. HpaII methylase was provided by Dr. K. Agarwal, University of Chicago, Chicago, Ill. T4 DNA polymerase was obtained form New England BioLabs. The use of T4 DNA polymerase and suitable reaction conditions have been previously described in copending application Ser. No. 125,878. Micrococcal S1 nuclease was obtained from Miles Laboratories, Elkhart, Ind. The use of S1 nuclease and suitable reaction conditions have been previously described by Ullrich, A., et al, supra. The Klenow fragment of DNA polymerase I was obtained from New England BioLabs. The use of the Klenow fragment of DNA polymerase I and suitable reaction conditions have been previously described by Klenow, H. and Hennigsen, I., *Proc. Nat. Acad. Sci. USA* 65, 168 (1970). Synthetic linker molecules were obtained from Collaborative Research, Inc., Waltham, Mass.

EXAMPLE 1

Plasmid ptrpED5-1 was prepared as described by Hallewell and Emtage, supra. 10 μg of ptrpED5-1 were digested with HinfI and the resulting fragments made flush-ended by a 10 minute incubation at 20° C. with the Klenow fragment of DNA polymerase I in a reaction volume of 20 μl containing 1 μl of the polymerase, 50 mM Tris pH7.5, 10 mM $MgCl_2$, 500 μM each of dATP, dTTP dCTP and dGTP and 10 mM 2-mercaptoethanol. The 500 base pair HinfI fragment containing the trp regulatory region was eluted from a 5% acrylamide gel and ethanol precipitated. The HinfI fragment was then ligated to a hundred-fold molar excess of synthetic HindIII linker molecules (d(pCCAAGCTTGG)) in a reaction volume of 30 μl containing 2 μl T4 DNA ligase, 50 mM Tris pH7.5, 10 mM $MgCl_2$, 10 mM dithiothreitol and 1 mM rATP at 15° C. for 16 hours. The ligase is inactivated by heat treatment at 68° C. for 5 minutes. The HindIII linker treated HinfI fragment was cut with HindIII, the mixture was extracted with phenol-chloroform and ethanol precipitated. Excess linker molecules and linker molecule fragments were removed from the HinfI fragment by chromatography on Sepharose TM CL 4B (Pharmacia, Inc., Uppsala, Sweden). The plasmid pBR322 was cut with HindIII, treated with aldaline phosphatase and the HinfI fragment inserted into the HindIII site by following the procedure described by Ullrich et al, supra. Host bacteria *E. coli* RRI were transformed by the resulting recombinant vector bearing the 500 base pair Hinf fragment and transformants were selected for resistance to ampicillin. A recombinant clone with the trp promoter directed towards the β-lactamase gene was obtained by screening DNA miniscreens for a 200 base pair HpaI-EcoRI fragment. This plasmid was designated ptrpE2-1.

A first portion of the plasmid ptrpE2-1 was digested with a mixture of HpaI and TaqI and a 34 base pair HpaI-TaqI fragment was purified by polyacrylamide gell electrophoresis. A second portion of the plasmid ptrpE2-1 was digested with a mixture of ClaI and HpaI. The ClaI-HpaI treated ptrpE2-1, i.e. ptrpE2-1 lacking a ClaI-HpaI fragment, was purified by polyacrylamide gel electrophoresis and then ligated to a three-fold molar excess of the purified HpaI-TaqI fragment using T4 DNA ligase following the procedure described by Ullrich et al, supra. Host bacteria *E. coli* HB101 were transformed by the resulting recombinant vector bearing the promoter, operator and leader ribosomal binding site of the trp operon. Transformants were selected for resistance to ampicillin. A recombinant clone was obtained by screening DNA miniscreens for a 34 base pair HpaI-ClaI fragment. This plasmid was designated ptrpL1. The plasmid was also found to contain a single ClaI site, a single HindIII site and the expected DNA sequence around the ClaI site.

EXAMPLE 2

Hepatitis B core antigen (HBcAg) gene was inserted into the expression vector ptrpL1 in order to demonstrate direct expression of a foreign gene.

A recombinant clone containing the entire hepatitis B virus DNA, as described by Valenzuela, P. et al, *Nature* 280, 815 (1979) and Valenzuela, P. et al, *Animal Virus Genetics*, Fields, B., Janenisch, R. and Fox, C. F., Ed., Academic Press, NY, 1980, was digested with HhaI. A 1005 base pair fragment containing the HBcAg gene was isolated by preparative acrylamide gel electrophoresis. 20 μg of the HhaI fragment were treated with HpaII methylase as described by Yoo, J. and Agarwall, K. L., *J. Biol. Chem.* 255, 6445 (1980). The fragment was then treated with 28 units of T4 DNA polymerase in the absence of deoxyribonucleotide triphosphates in 30 mM Tris-acetate, 67 mM K-acetate, 10 mM Mg-acetate, 0.5 mM dithiothreitol, and 100 μg/ml bovine serum albumin for 30 seconds at 37° C. in order to remove nucleotides from the 3' ends. This reaction produced fragments containing the HBcAg gene and having 5–20 base pairs separating the end of the fragments and the start codon. The reaction was stopped by the addition of phenol. The DNA was extracted with chloroform: isoamyl alcohol (24:1) and precipitated with ethanol. The resulting fragment was then treated with S1 nuclease and BamHI linker molecules (d (pCCGGATCCGG)) ligated thereto as described by Ulrich et al, supra. The BamHI linker treated fragment was cut with HpaII, the mixture extracted with phenol-chloroform and precipitated with ethanol. The fragment containing the HBcAg gene was purified from the digested linkers by preparative acrylamide gel electrophoresis. The plasmid ptrpL 1 was cut with ClaI, treated with alkaline phosphatase and the fragment inserted therein following the procedure described by Ulrich et al, supra. Host bacteria HB101 were transformed by the resulting recombinant vector bearing the HBcAg gene. Transformants were selected on L plates (Miller, J. H., in *Experiments in Molecular Genetics*, Appendix I, Cold Spring Harbor Laboratory, Cold Spring Harbor, N.Y., (1972)) containing 20 μg/ml ampicillin and screened for recombinants using a modified toothpick assay (Barnes, W. B., *Science* 195, 393 (1977)). Forty such recombinants were then tested for HBcAg using a double antibody radioimmune assay with human anti-HBcAg (Ling, C. M. and Overbey, L. R., *J. Immunol.* 109, 834 (1972)). Seventeen of these recombinants were positive for HBcAg. Restriction enzyme analysis of the plasmids showed that all seventeen contained the HBcAg gene sequence and all were in proper orientation for trp-dependent expression of HBcAg. Four of these plasmids were analyzed by DNA sequence analysis. It was found that the distance between the leader ribosomal binding site and the start codon of the HBcAg gene varied from 12–15 base pairs. The plasmid producing the highest level of HBcAg was identified as ptC246.

Figure 2:
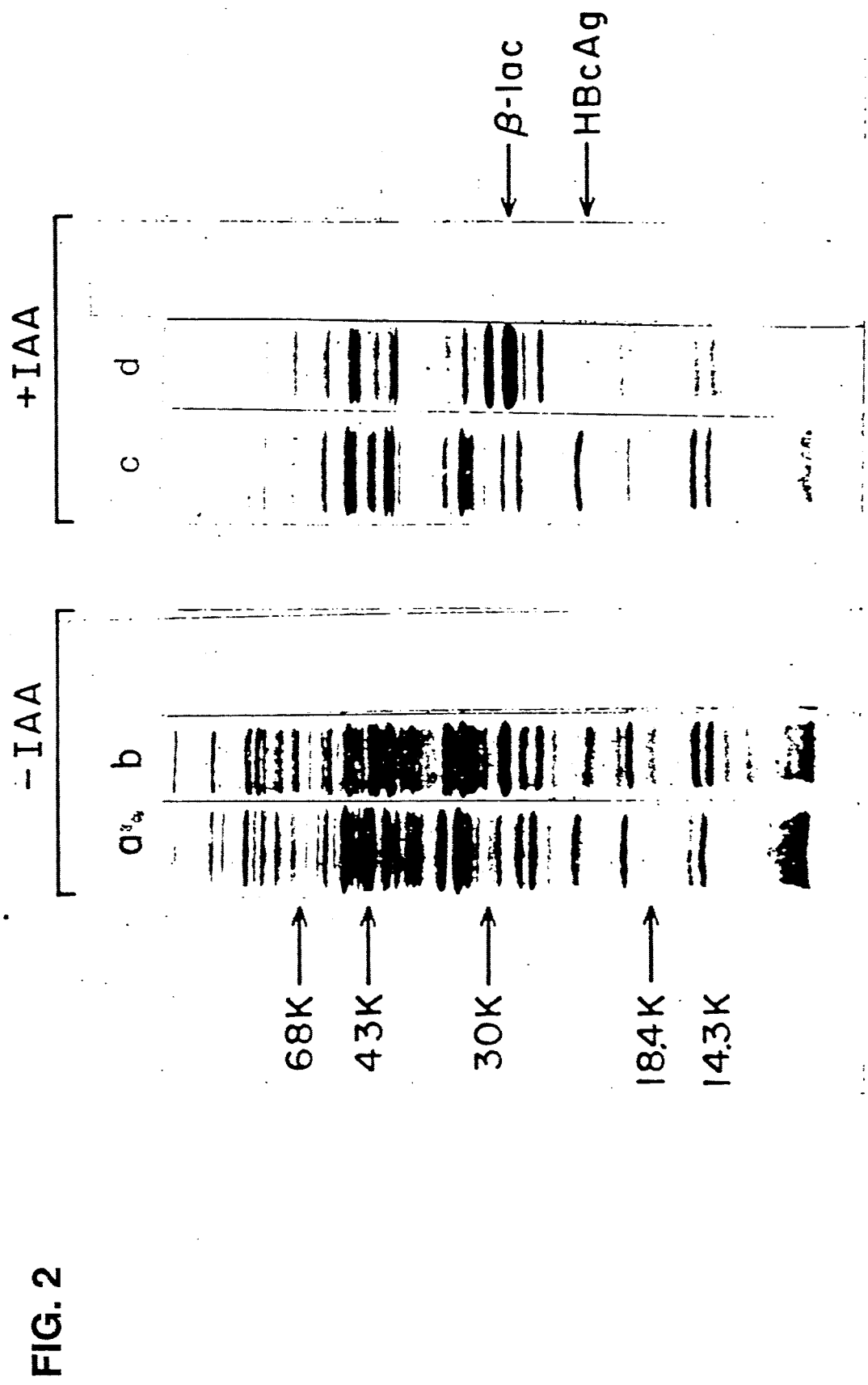

Cells containing ptC246 were cultured overnight in M9 media (Miller, J. H., supra) containing 0.25% casamino acids, 0.5% glucose and 0.01% B1. The cultures were diluted 1:10 with fresh media, grown for 1 hour at 30° C., 15 μg/ml of 3-β-indolylacrylic acid was added, and the cultures grown for another 2 hours at 30° C. Cultures in which 3-β-indolylacrylic acid was not added were used as controls. The cultures were then labelled for 20 minutes at 30° C. with 10 μCi/ml of $^{35}$S-cysteine. The protein products were electrophoresed on sodium dodecylsulfatepolyacrylamide gels and the protein bands were visualized by autoradiography. The results, as seen in FIG. 2, show the presence of a new protein band of about 22,000 daltons present in lower levels in the uninduced cells FIG. 2 lanes a and c.

These bands were not present in cells that did not contain the plasmid ptCA246. FIG. 2, lanes b and d. The DNA sequence of the HBcAg gene predicts a protein of molecular weight of 21,105 daltons (Valenzuela, P. et al, Animal Virus Genetics, supra). Cultures of ptrpL1-containing cells were also treated as above. Protein bands from noninduced and induced cells are shown in FIG. 2 lanes b and d, respectively.

Figure 3:
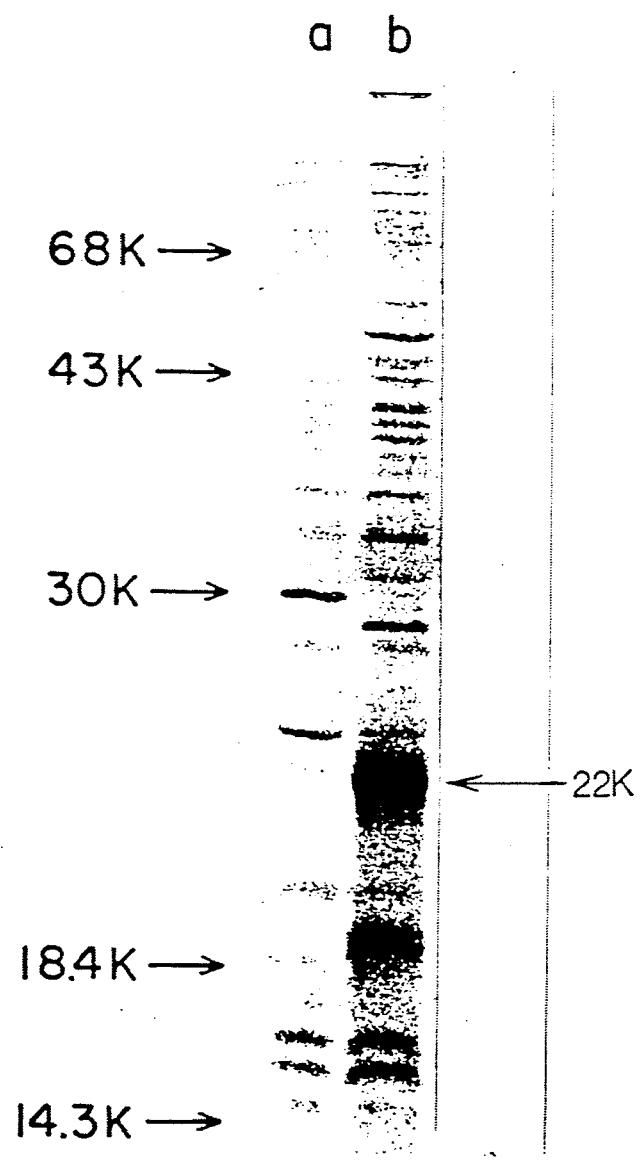

Cells were grown and labelled with $^{35}$S-cysteine as described above. The labelled cells were collected by centrifugation and resuspended in phosphate-buffered saline containing 1 mM phenylmethylsulfonylfluoride. The cells were sonicated and proteins immunoprecipitated with anti-HbcAg serum (FIG. 3 lane b) or normal IgG as the control (FIG. 3, lane a) using the SAC technique described by Martial, J. A. et al, *Science* 205, 602 (1979). The predominant band is the 22,000 dalton polypeptide as shown in FIG. 3. Lane b; no band is seen in FIG. 3, Lane a. FIGS. 2 and 3 clearly show that HBcAg is produced by transformed cells, that HBcAg is produced directly and not as a fusion protein, and that production of HBcAg is under control of the trp promoter and operator.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

On Dec. 5, 1980, the following materials were deposited with ATCC (Rockville, Md.). These deposits comply with the terms of the Budapest Treaty, and are also available without restriction. Availability of these deposits is not to be construed as a license to practice the invention in contravention of rights granted by any nation under authority of its patent laws. *E. coli* HB101/ptCA246 (ATCC 31755) *E. coli* HB101/ptrpL1 (ATCC 31757).

What is claimed is:

1. A recombinant DNA transfer vector suitable for the direct expression of a foreign DNA sequence having a start codon, which vector comprises (a) a portion of the trp operon consisting essentially of the promoter, operator, leader ribosome binding site, and (b) a restriction site providing the insertion site for said foreign DNA sequence wherein said restriction site is a ClaI site and is located within 50 nucleotides 3' of the ribosome binding site.

2. The transfer vector of claim 1 comprising the DNA sequence of the promoter, operator and leader ribosome binding site and a restriction site, said restriction site comprising a DNA sequence recognized by ClaI restriction endonuclease comprising the sequence:

5'-TTAACTAGTACGCAAGTTCACG-
TAAAAAGGGTATCGAT-3'
3'-AATTGATCATGCGTTCAAGT-
GCATTTTTCCCATAGCTA-5', wherein
A is deoxyadenyl,
G is deoxyguanyl,
C is deoxycytosyl and
T is thymidyl.

3. The plasmid of claim 2, which is ptrpL1.

4. An *Escherichia coli* strain HB101 transformed by the transfer vector of claim 1.

* * * * *